United States Patent [19]
Nakamura et al.

[11] Patent Number: 5,445,633
[45] Date of Patent: Aug. 29, 1995

[54] ABLATION APPARATUS FOR ABLATING A CORNEA BY LASER BEAM

[75] Inventors: Takua Nakamura; Toshifumi Sumiya, both of Aichi, Japan

[73] Assignee: Nidek Co., Ltd., Aichi, Japan

[21] Appl. No.: 329,673

[22] Filed: Oct. 25, 1994

Related U.S. Application Data

[63] Continuation of Ser. No. 15,924, Feb. 10, 1993, abandoned.

[30] Foreign Application Priority Data

Nov. 7, 1992 [JP] Japan .................................. 4-322387
Nov. 7, 1992 [JP] Japan .................................. 4-337929

[51] Int. Cl.$^6$ .......................... A61B 17/00; A61N 5/06
[52] U.S. Cl. ............................................. 606/5; 606/4
[58] Field of Search ................. 606/4, 5, 6, 10, 11, 606/12; 128/898

[56] References Cited

U.S. PATENT DOCUMENTS

| | | | |
|---|---|---|---|
| 4,732,148 | 3/1988 | L'Esperance, Jr. | 606/5 |
| 4,911,711 | 3/1990 | Telfair et al. | 606/5 |
| 4,941,093 | 7/1990 | Marshall et al. | 606/5 |
| 4,994,058 | 2/1991 | Raven et al. | 606/5 |

FOREIGN PATENT DOCUMENTS 63-289519  11/1988  Japan .

OTHER PUBLICATIONS

Japanese Patent Application No. Hei. 2-416767 which corresponds to U.S. patent application Ser. No. 07/812,819, a copy of the specification of which is filed herewith.

Primary Examiner—Stephen C. Pellegrino
Assistant Examiner—Sonya C. Harris
Attorney, Agent, or Firm—Finnegan, Henderson, Farabow, Garrett & Dunner

[57] ABSTRACT

An ablation apparatus for ablating the surface of a cornea by laser beam having a laser source for emitting a laser beam, an ablation optical system for ablating the surface of a cornea by the laser beam emitted from the laser source, an diaphragm with a variable diameter for changing an ablation area on the cornea, a cornea shape forming device for forming a desired shape of cornea's optical zone by superposing the irradiation through the ablation optical system, an input device for inputting a data to determine a transition zone as to be connected the optical zone with a non-ablation area smoothly, and a control device for controlling the diameter of the diaphragm by determining the shape of the transition zone based on the data inputted through the input device.

11 Claims, 12 Drawing Sheets

WIDTH OF TRANSITION ZONE
ΔY(x)
DEPTH OF ABLATION FOR TRANSITION ZONE
POST-CURVE
TRANSITION ZONE-CURVE
PRE-CURVE

ABLATION APPARATUS FOR ABLATING A CORNEA BY LASER BEAM

This application is a continuation of application Ser. No. 08/015,924 filed Feb. 10, 1993, now abandoned.

BACKGROUND OF THE INVENTION

1. Field of the Invention

The present invention relates to an ablation apparatus for ablating an object by laser beam, more particularly, relates to an ablation apparatus for controlling ablation of a surface of a cornea by laser beam to correct the curvature of the cornea and/or for removing the regional lesion portion thereof.

2. Description of Related Art

Recently, some methods have been proposed for correcting the refraction of an eye by ablating the surface of the cornea by laser beam (generally an excimer laser having an wavelength 193 nm is employed, also YAG laser and the like is tried to be used.) to change the curvature of the cornea. In these methods, it is necessary to control the depth of the ablation area so that it is uniform. This has been accomplished by controlling the intensity distribution of the laser beam being used for ablation such that it is constant.

For example, U.S. patent application Ser. No. 07/812,819 filed on Dec. 24, 1991, based on Japanese Patent Application No. HEI 2-416767, proposes the method for controlling the depth of the ablation by employing an excimer laser beam having an uniform beam intensity in one direction and a non-uniform beam intensity of Gaussian distribution in the vertical direction, and by scanning the laser beam into the Gaussian distribution direction by using optical elements.

In this kind of ablation mechanism, the refraction of the cornea such as myopia or astigmatism is corrected by restricting the irradiation area by employing a variable circular diaphragm or a variable slit diaphragm or the like, or by employing a special filter for changing a character of the beam transmission factor.

The operation method of removing the regional lesion portion of the cornea partially is known. This operation has a special character in restriction method of the irradiation area or positioning between the optical axis and the examinee's eye.

In the above mentioned ablation, correcting the refraction of the cornea or the removal of regional lesion portion thereof may be effectively operated. However, the boundary between the ablation area and the non-ablation area is appeared in a condition of making a clear height-difference. Therefore, not only is there a problem in the appearance, but also some dangers in that the opacity of the cornea or the like occurs without making the epithelium regeneration smoothly.

According to ablation which strips the corneal epithelium wider more than the optical zone after the operation, the epithelium regeneration proceeds from the outside of the optical zone toward the inside thereof. But if there are extreme changes of the curvature at the boundary area between the ablation area and the non-ablation area, epithelium regeneration is affected badly.

SUMMARY OF THE INVENTION

Accordingly, it is an object of the present invention to overcome the above problems and to provide an ablation apparatus for ablating a cornea by laser beam to obtain a smoothly curved surface of the boundary between the ablation area and the non-ablation area and also to obtain a corneal epithelium regeneration smoothly.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

The above and further objects and novel features of the invention will be attained by an ablation apparatus for ablating the surface of a cornea by a laser beam comprising a laser source for emitting a laser beam, an ablation optical system for ablating the surface of a cornea by the laser beam emitted from the laser source, an ablation area changing means for changing an ablation area on the cornea, a cornea shape forming means for forming a desired shape of cornea's optical zone by superposing the irradiation through the ablation optical system, an input means for inputting a data to determine a transition zone as to be connected the optical zone with a non-ablation area smoothly and a control means for controlling the movement of the ablation area changing means by determining the shape of the transition zone based on the data inputted through the input means.

Further, an ablation apparatus for ablating the surface of a cornea by laser beam comprises a laser source for emitting a laser beam, an ablation optical system for irradiating the laser beam emitted from the laser source onto the surface of a cornea, an ablation area confining means for confining an ablation area on the cornea, the confining means being disposed in the ablation optical system, an ablation area changing means for changing the ablation area on the cornea confined by the ablation area confining means, a transition zone's form determining means for determining the sectional form of a transition zone which is formed between the ablation area and non-ablation area, and an ablation area control means for controlling the ablation area on the cornea changed by the ablation area changing means as to be obtained the shape of transition area smoothly connected with optical zone and non-ablation area.

BRIEF DESCRIPTION OF THE DRAWINGS

The invention will be described in detail with reference to the following drawings, wherein:

FIG. 3(a) through 3(d) are diagrams showing the laser beam intensity profile in the vertical (Y-axis) direction on an diaphragm;

FIG. 4(a) through 4(d) are diagrams showing the laser beam intensity profile in the vertical (Y-axis) direction on the cornea of an eye;

FIG. 5(a) through 5(e) are diagrams to explain the condition (process) of ablation of FIG. 4;

DETAILED DESCRIPTON OF THE PREFERRED EMBODIMENTS

A detailed description of a preferred embodiment of an ablation apparatus embodying the present invention will now be given referring to the accompanying drawings.

Figure 1:
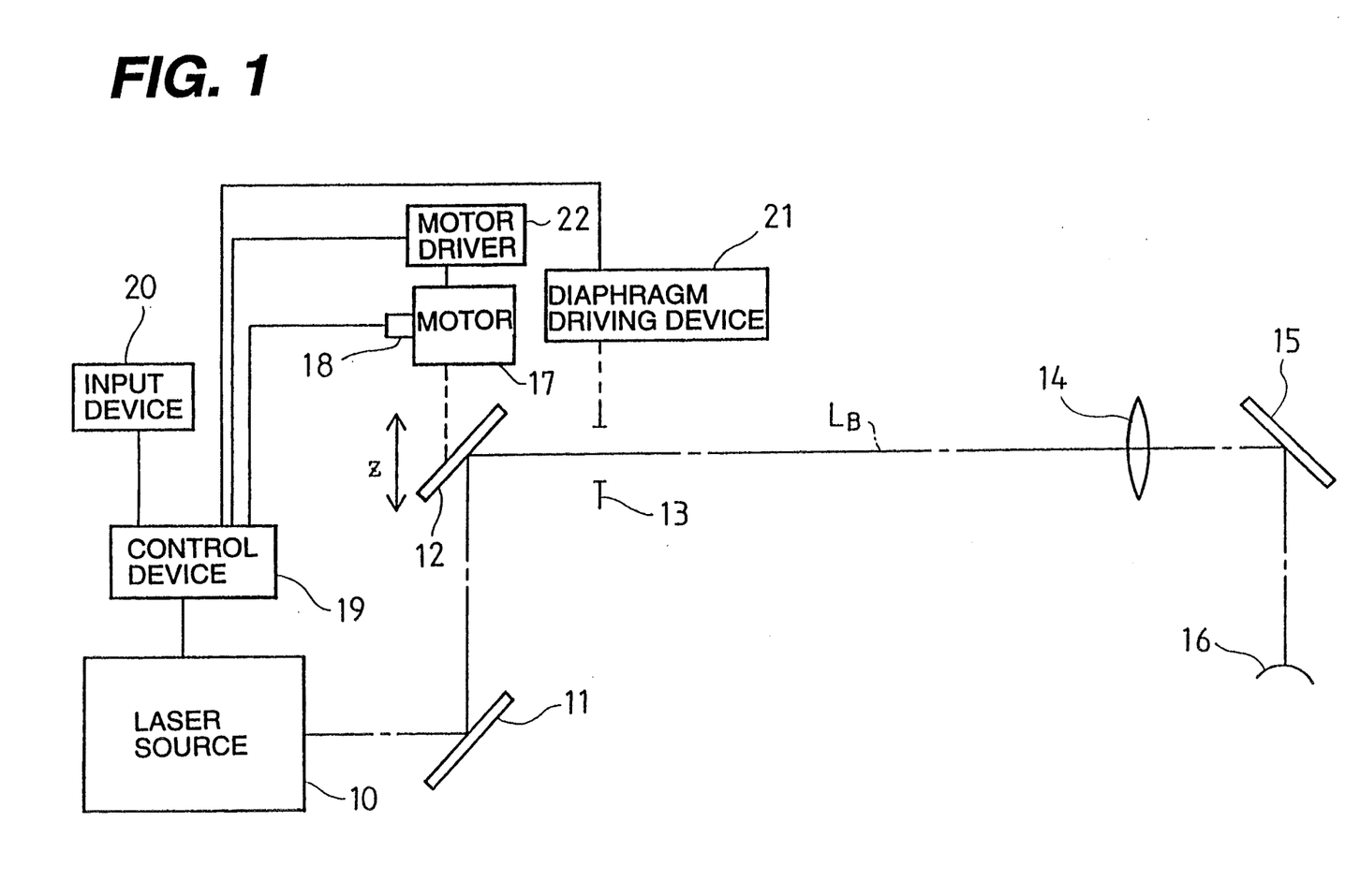
FIG. 1 is a schematic diagram of the arrangement of optical components of the first embodiment explaining the present invention.

As shown in FIG. 1, an optical system of the ablation apparatus includes a laser source 10 (preferably an excimer laser, plane mirrors 11, 12, 15 for deflecting the laser) beam $L_B$ emerging from the laser source 10, an diaphragm 13 with a variable diameter located in the optical path between the mirrors 12, 15, and a projection lens 14 for projecting the laser beam $L_B$ passing through the diaphragm 13 to a cornea 16 via mirror 15.

The laser beam $L_B$ emerging from the laser source 10 is deflected 90° by the plane mirror 11 and another 90° by the mirror 12 while it remains in the same plane. After the laser beam passes through the diaphragm 13, the laser beam $L_B$ is also deflected 90° by the plane mirror 15 in the same plane, and projected to the surface of the cornea 16.

The projection lens 14 is conjugated with the diaphragm 13 and the cornea 16, and the laser beam passing through the aperture confined by the diaphragm 13 in a confined space is projected on the surface of the cornea 16 such that an ablation area of the cornea is restricted.

The cornea is provided at a position having a predetermined positioning relation for the apparatus.

Figure 2:
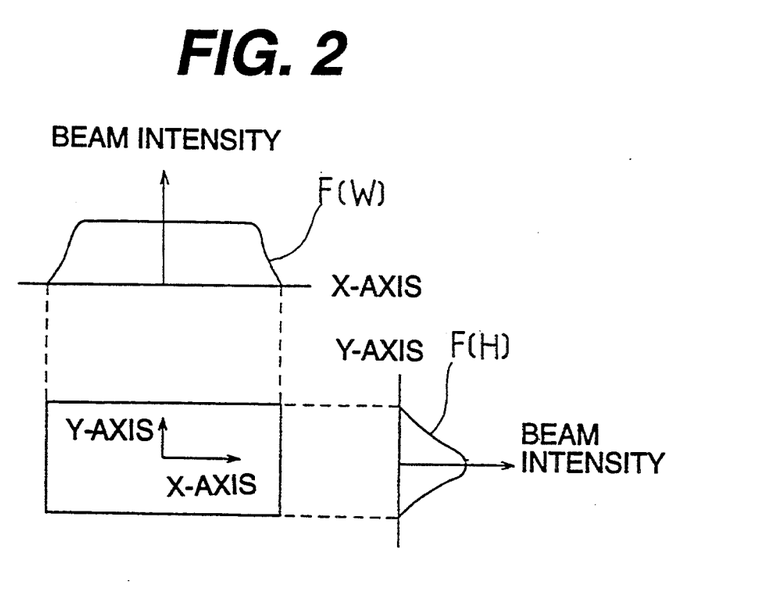
FIG. 2 is a schematic diagram of a horizontal (X-axis) beam intensity profile and a vertical (Y-axis) beam intensity of a laser beam from an excimer laser as used in the embodiment of FIG. 1.

The beam section profile of the laser beam emitted from the laser source 10 of FIG. 1, has an almost uniform intensity distribution F(W) in the horizontal direction (X-axis direction) of the laser beam, but the beam intensity distribution in the vertical direction (Y-axis direction) is a Gaussian distribution F(H) as shown in FIG. 2.

The plane mirror 12 of FIG. 1, is movable parallel to the Z-axis by a driving motor 17, and the position of the mirror 12 (amount of movement) is detected by a positioning detector 18. The positioning detector 18 may comprise, for example, a rotary encoder attached to a driving axis of the mirror's driving motor 17.

The positioning detector 18 and the laser source 10 are connected to a control device 19, and the laser pulses are emitted based on an output signal of the positioning detector 18. The operation of the present apparatus is controlled by a microcomputer of the control device 19.

That is, an input device 20 is connected to the control device 19, and datum including radius of curvature of the pre-ablation cornea, correction power of an eye, size of the optical zone and the transition zone which is the boundary area between the ablation area (exactly optical zone) and the non-ablation area, the width of the transition zone and the depth of the ablation to be taken place or the like, are inputted via the input device 20.

And also, a diaphragm driving device 21 for changing a diameter of the diaphragm 13 is connected to the control device 19, and the diameter of the diaphragm 13 is changed based on an output signal of the control device 19. Numeral 22, in FIG. 1, is a motor driver connected to the motor 17, and the motor driver 22 drives the motor 17 based on an output signal of the control device 19.

As described above, the mirror 12 moves parallel to the Z-axis direction of FIG. 1, whereby the laser beam is moved in parallel in the direction of the Gaussian distribution. The plane mirror 12 moves synchronously to the laser pulse outputted by laser source 10, and after one or more laser pulses have been outputted at a certified position of the plane mirror 12, the mirror 12 moves to a next position, and again at that position of the mirror 12 one or more laser pulses will be further outputted as the mirror 12 moves further to a next position. This moving operation is repeated from the one end of the diaphragm 13 to the other end. This means that the irradiation of the laser beam is repeated on the ablation area of the cornea 16 at a determined interval (by one or more of the laser pulses) so that the pulses are combined and a uniform depth of ablation is achieved.

The moving amount of the plane mirror 12 is determined by correlation among several components, e.g., the depth of ablation, the degree of uniformity required or the intensity and intensity distribution of the laser beam and the like. The adjustment of the laser beam's intensity or the ablation's depth per one pulse may be obtained by adjusting the output power of the laser source within a certain range.

For convenience of explanation, it may be assumed that the plane mirror 12 moves for every pulse although such a one-to-one relationship is not required for the present invention. FIGS. 3(a) through 3(d) show the change of the intensity distribution of the laser beam in Y-axis direction on the diaphragm 13. FIGS. 4(a) through 4(d) show the change of the intensity distribution in the Y-axis direction on the cornea 16. FIGS. 5(a) through 5(e) show the condition (process) of the ablation on the cornea.

Figure 3A:
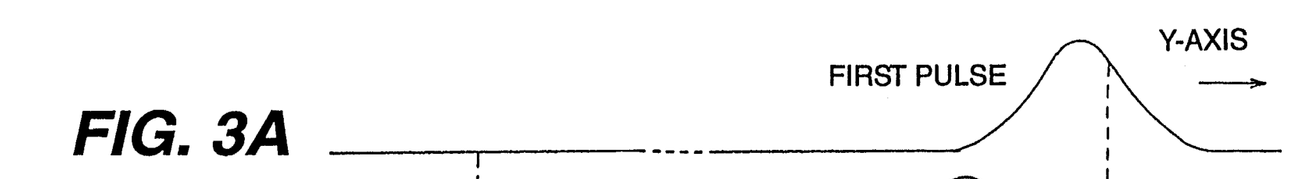
Figures 3B, 3C:
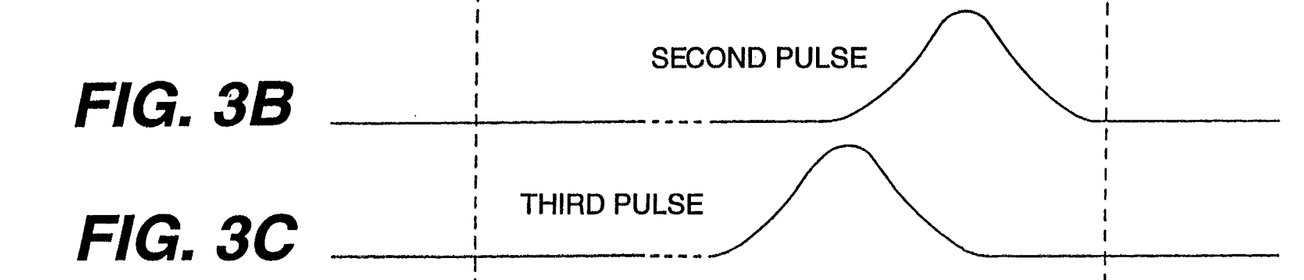
Figure 3D:
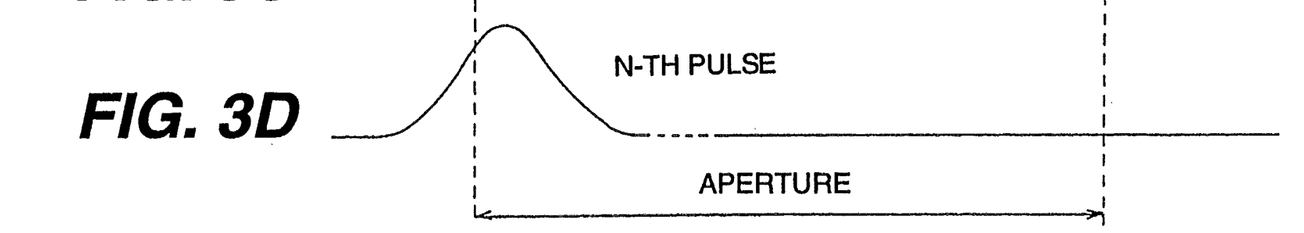
Figures 4A, 4B, 4C, 4D:
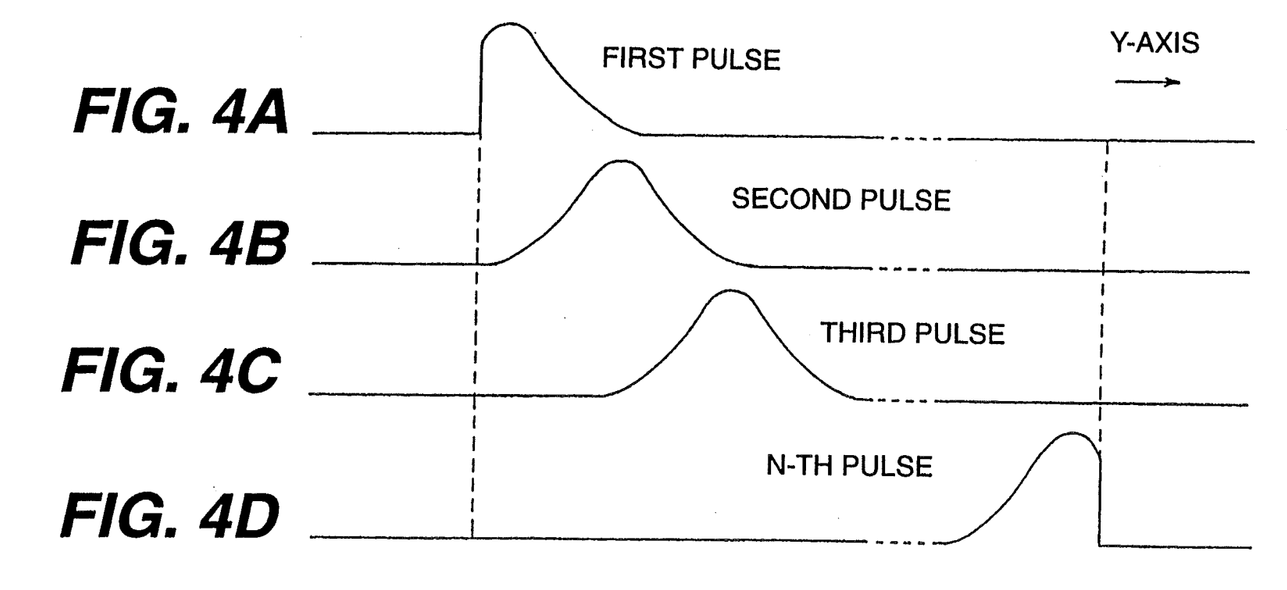
Figures 5A, 5B, 5C, 5D, 5E:
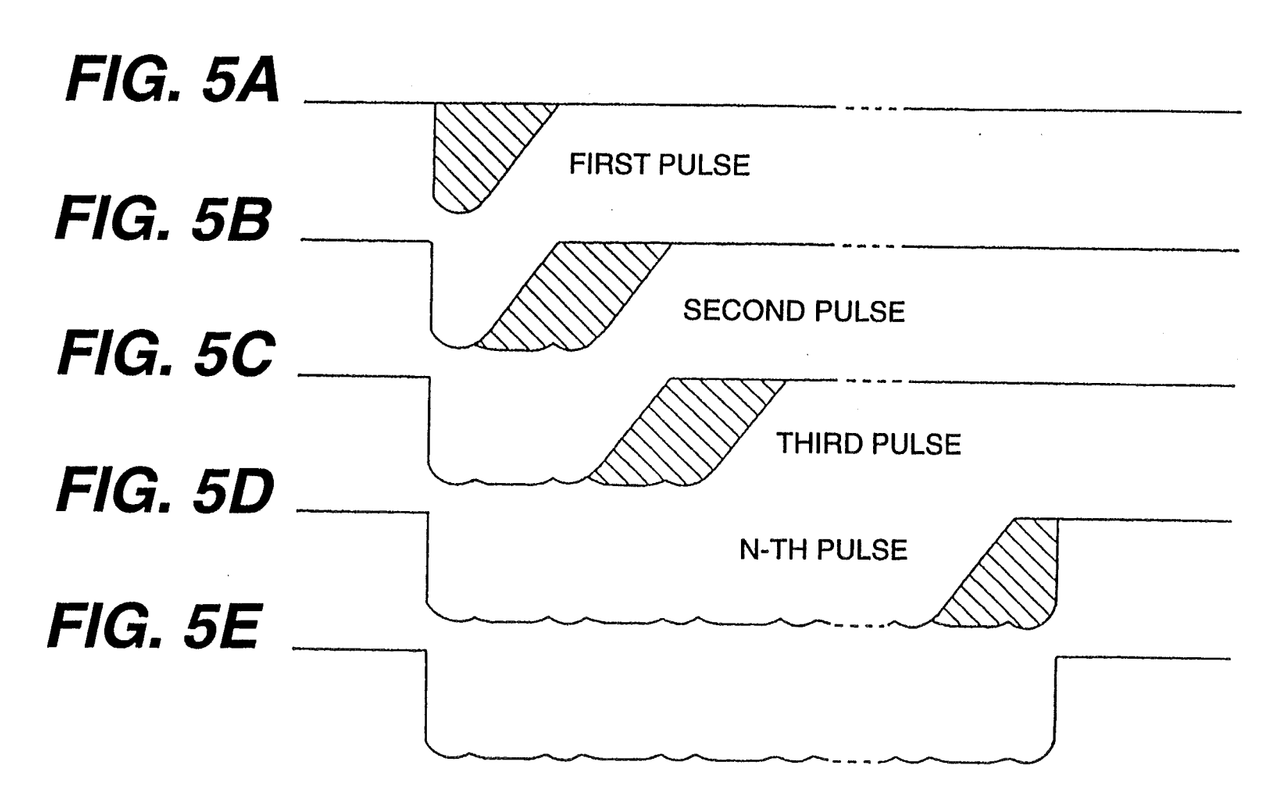

When a first pulse of the laser beam having the intensity distribution shown in FIG. 3(a) on the diaphragm 13 is irradiated on the cornea 16 by the projection lens 14, the intensity distribution on the cornea 16 is as shown in FIG. 4(a). At that time, the cornea 16 is ablated by the irradiation of the laser beam, as shown with oblique lines in FIG. 5(a). When a second pulse of the laser beam is irradiated, as the plane mirror 12 has been moved in the Z-axis direction, the intensity distribution on the diaphragm 13 is changed as shown in FIG. 3(b). Accordingly, the intensity distribution projected on the cornea 18 by the projection lens 14 is as shown in FIG. 4(b), and the cornea 16 is further ablated as shown with oblique lines in FIG. 5(b). The third pulse of the laser beam produces an intensity distribution on the diaphragm 13 as shown in FIG. 3(c) and the intensity distribution on the cornea 16 as shown in FIG. 4(c), whereby the area of the cornea shown with oblique lines in FIG. 5(c) is further ablated. The fourth and the subsequent laser pulses up to the n-th pulse of the laser beam, cause an intensity distribution on the diaphragm 13 as shown in FIG. 3(d). FIG. 4(d) shows the intensity distributions on the cornea 16 and the area shown in FIG. 5(d) with oblique lines is ablated.

By moving the plane mirror 12 parallel to the Z-axis direction synchronously with respect to the laser pulse and irradiating the laser beam while scanning it in the direction of its non-uniform intensity distribution, the cornea 16 is ablated with an almost uniform depth shown in FIG. 5(e).

As proposed in Japanese Patent Application No. HEI 4-286999 (The title of the invention: Ablation Apparatus By Laser-Beam) by the applicant of the present invention, by disposing an image-rotator on the optical path and by rotating a beam direction, the problem of the dispersion of the intensity distribution by lack of adjustment of a laser resonator is settled.

Figure 6A:
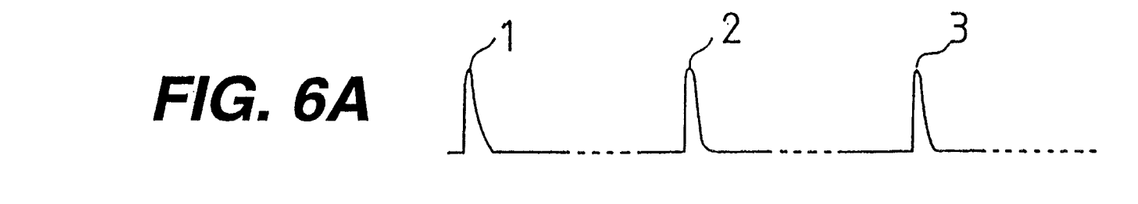
FIG. 6(a) and 6(b) are timing charts to explain the movement control of the plane mirror 12 shown in FIG. 1 with respect to the laser pulse.
Figure 6B:
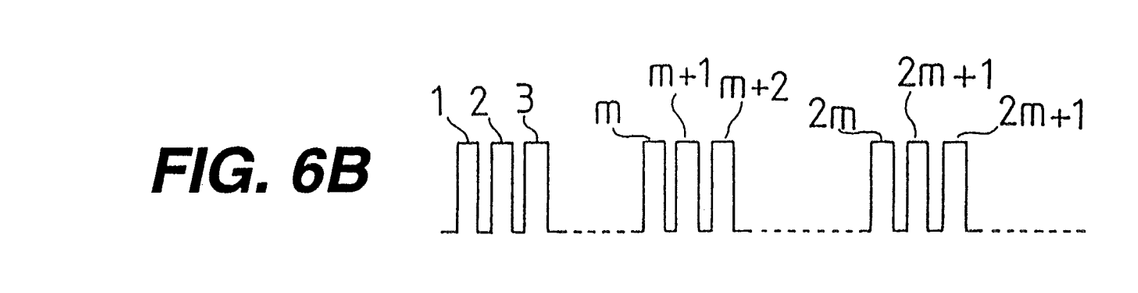

FIGS. 6(a) and 6(b) are timing charts to explain the timing of a control mechanism that moves the plane mirror 12 synchronously with respect to the laser pulses. In the FIG. 6(a), the output pulse of the laser beam is shown and FIG. 6(b) shows output signals of the detector 18 detecting the position of the plane mirror 12.

The amount of movement of the plane mirror 12 to obtain a uniform ablation depth employs an m-pulse output signal of the position detector 18.

If the output signal of the position detector 18 detecting the position of the plane mirror 12 at the time of the first laser beam pulse is the first detecting pulse, the plane mirror 12 is moved so that the m+1-th output signal is outputted at the time of the second laser pulse and 2m+1-th output signal is outputted at the time of the third laser pulse so that the laser pulse is emitted each m-th pulse of the output signal of the position detector 18. By repeating such laser beam pulses, uniform ablation by the laser beam irradiation is accomplished. It is proper that the laser is used in a condition of about 50 Hz, so that operation time is shortened and the load of the laser should be decreased.

The above description of the embodiment describes a relation of the direction of the laser beam's energy distribution, and other directions may be employed.

By employing the above mentioned apparatus, the method of forming the transition zone to obtain a smooth surface without height difference around the ablation area is explained as follows.

The first method is for removing a regional lesion portion of the eye, too. In case of the lesion's removing, it is exchangeable from the circular diaphragm to the variable slit diaphragm.

In this method, the shape of the transition zone is obtained by dividing into three cases, in consideration of the existence of the legion removing deeply.

The first case is one that the depth of the ablation is smaller than the width of the transition zone relatively as expressed in formula (1).

$$d \leq (\sqrt{2} - 1) W \quad (1)$$

W: width of transition zone
d: depth of ablation

These datum (W, d) are inputted into the apparatus via the input device 20 previously.

Figure 7:
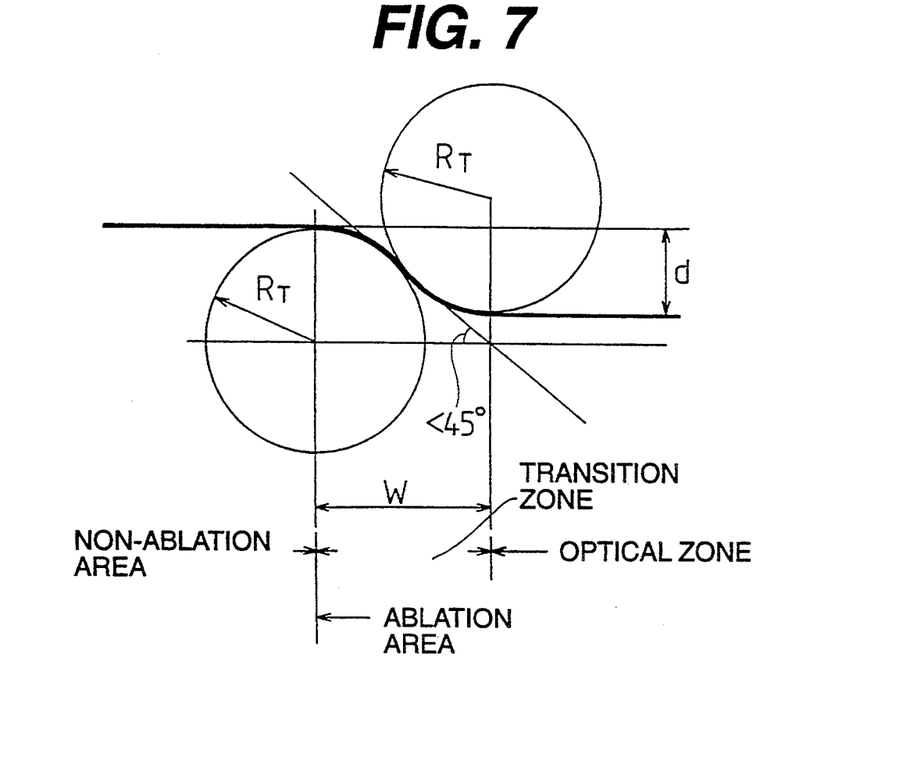
FIG. 7 is a diagram to explain the first method to form the transition zone between the ablation area of the cornea and the non-ablation area thereof, which shows the first case that the depth of the ablation is relatively slight to the width of the transition zone.

FIG. 7 shows the sectional form of the transition zone in case of formula (1). As shown in FIG. 7, the two circles with a radius of $R_T$ are bordered on each other between ablation area and non-ablation area, and the inclination of normal line passing through a tangent point is below 45 degrees. And the sectional form of the transition zone is formed along with each circle's curve so that the surface form of the transition zone becomes as smooth as possible. In the transition zone, the sectional form after ablation is shown with a bold line in FIG. 7, and is established to be point symmetry at central position W/2.

In FIG. 7, $R_T$ is obtained according to the following formula (2).

$$R_T = \frac{1}{4d} (W^2 + d^2) \quad (2)$$

The second case is one that the depth of the ablation is near to the width of the transition zone relatively as expressed in formula (3).

$$(\sqrt{2} - 1)W < d < W \quad (3)$$

Figure 8:
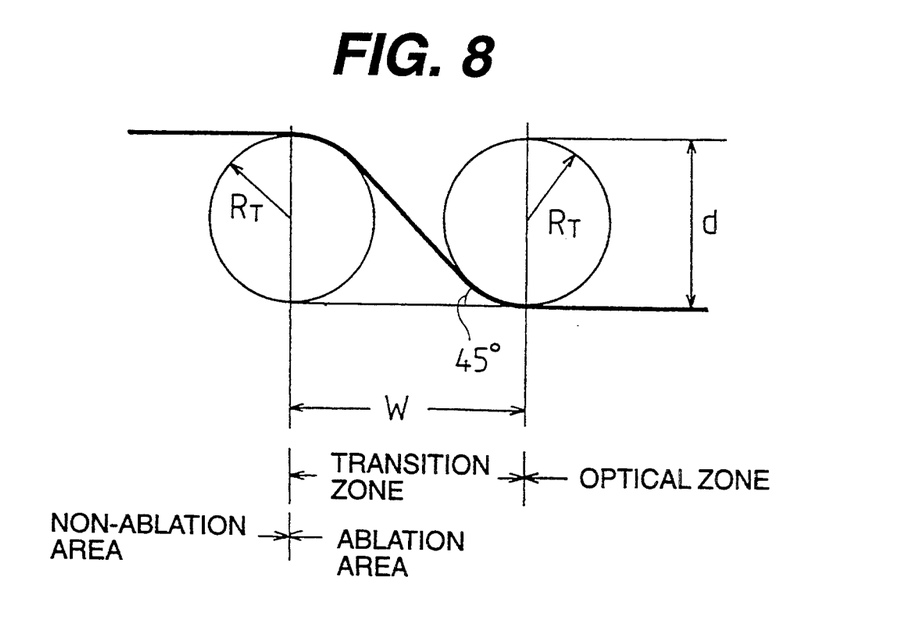
FIG. 8 is a diagram to explain the second method to form the transition zone between the ablation area of the cornea and the non-ablation area thereof, which shows the second case that the relation of between the depth of the ablation and the width of the transition zone takes a middle position.

The sectional form of the transition zone, as shown in FIG. 8, consists of two curves which is formed along with the two circles with a radius of $R_T$ positioned at a little bit distance each other and a straight line which is made by connecting tangent points of the circles, the inclination of the straight line is 45 degrees. In this case, $R_T$ is obtained according to the following formula (4).

$$R_T = \frac{1}{2} (\sqrt{2} + 1)(W - d) \quad (4)$$

But when d=W, the radius $R_T$ of each circle is d/2.

The third case is one that the depth of the ablation is larger than the width of the transition zone relatively as expressed in formula (5).

$$W \leq d \quad (5)$$

Figure 9:
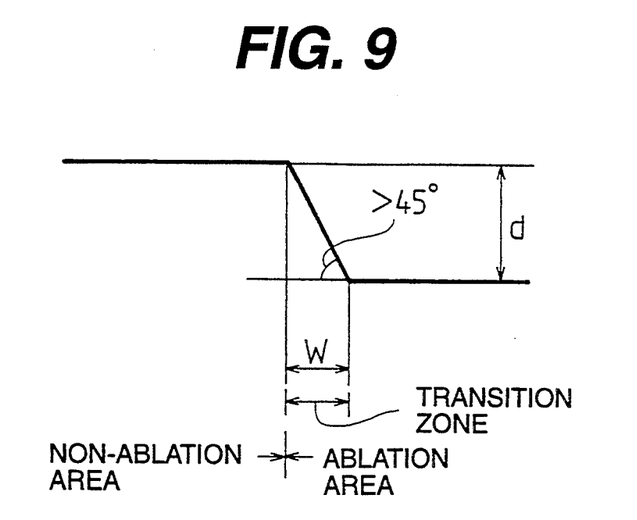
FIG. 9 is a diagram to explain the third method to form the transition zone between the ablation area of the cornea and the non-ablation area thereof, which shows the third case that the depth of the ablation is relatively deep to the width of the transition zone.

The sectional form of the transition zone is as shown in FIG. 9, that is, expressed by straight line. In case of forming the above mentioned transition zone, the relation of the diameter of circular diaphragm (or the width of slit diaphragm) and the number of steps is explained as example case of the above formula (1).

Figure 10:
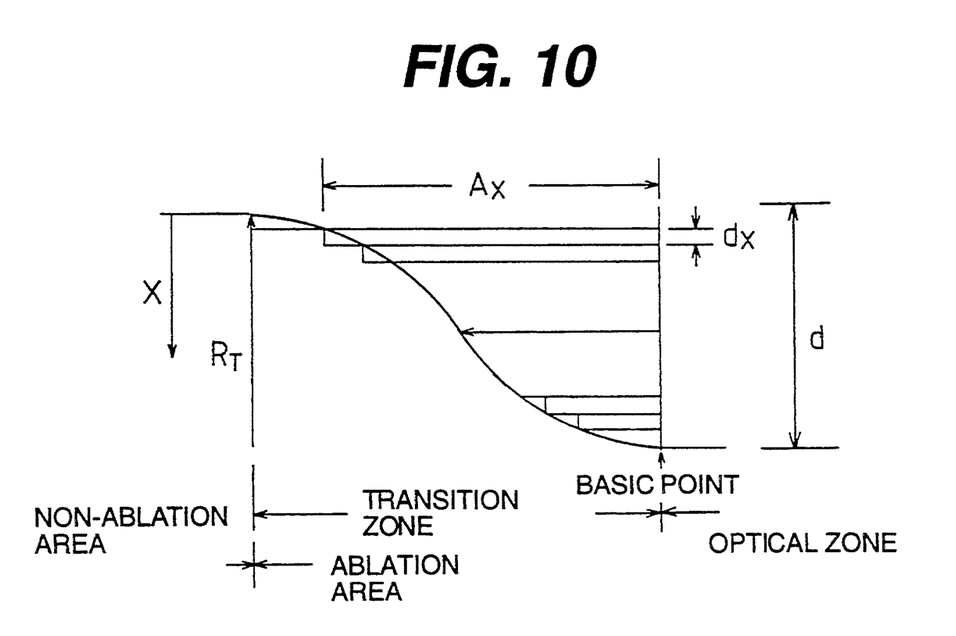
FIG. 10 is a diagram to explain the relation of between the diameter of the circular diaphragm (or the width of the slit diaphragm) and the number of steps.

And in case of formula (1), as is shown in FIG. 10, if each sign shows as follows:
W: the width of transition zone
$R_T$: the radius of curvature
d: total ablation's depth
$d_x$: the depth of each scanning ablation $A_x$: fitting position (distance from basic point to the end of aperture toward wide direction) the fitting position $A_x$ of when the depth of ablation is X, is shown as follows:

In case of $x \leq d/2$ $$A_x = \sqrt{\left(\frac{1}{2d}(W^2 + d^2) - x\right)x} \quad (6)$$

In case of $x > d/2$ $$A_x = W - \sqrt{\left(\frac{1}{2d}(W^2 + d^2) - (d - x)\right)(d - x)} \quad (7)$$

The surface of the cornea is ablated by the beam emitted from the laser source 10 via the mirror 12 which is parallel-scanned toward the z-axis direction in FIG. 1. And it is finished to scan on the surface of the cornea one scanning, that is, the depth of $d_x$ is ablated. By making narrow the diameter of the diaphragm, the ablation is proceeded gradually and deeply, whereby the expected ablation having the form of curvature as mentioned in the first case is obtained.

The second method forms the transition zone which is suitable to correct the myopia.

In this case, also the radius of curvature of the pre-ablation cornea, the correction power of the eye, the range of the optical zone and the range of the transition zone are inputted into the computer via the input device 20.

The second method is one to connect the optical zone of the ablation area and the non-ablation area smoothly by forming the transition zone with curved surface inscribed to both of the curved surfaces of pre-operation and post-operation.

Figure 11:
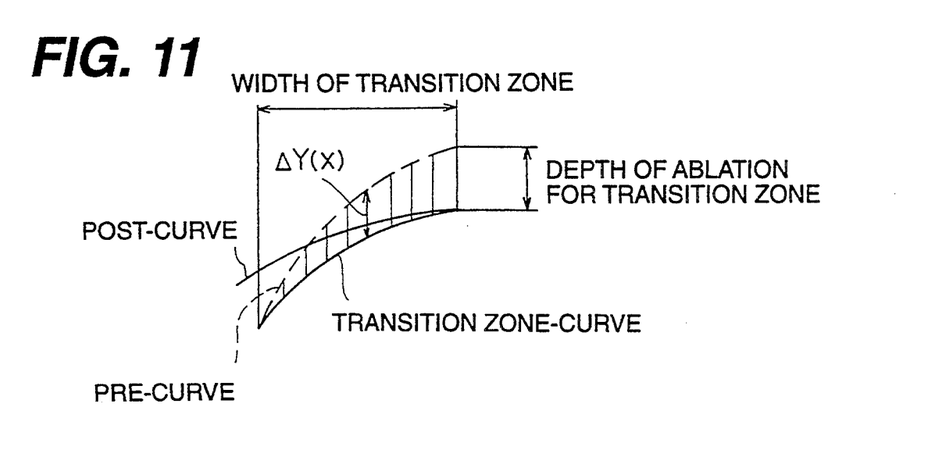
FIG. 11 is a diagram to explain the suitable shape of the transition zone formed around the optical zone in case of the correcting of the myopia.

In FIG. 11, as the pre-ablation curve of the cornea and the post-ablation curve thereof are decided, the curve of the transition zone is determined by obtaining a circle which is inscribed to both curved forms of pre- and post- operation and the depth of ablation $\Delta Y(x)$ toward each direction of diameter is obtained as datum.

Figure 12:
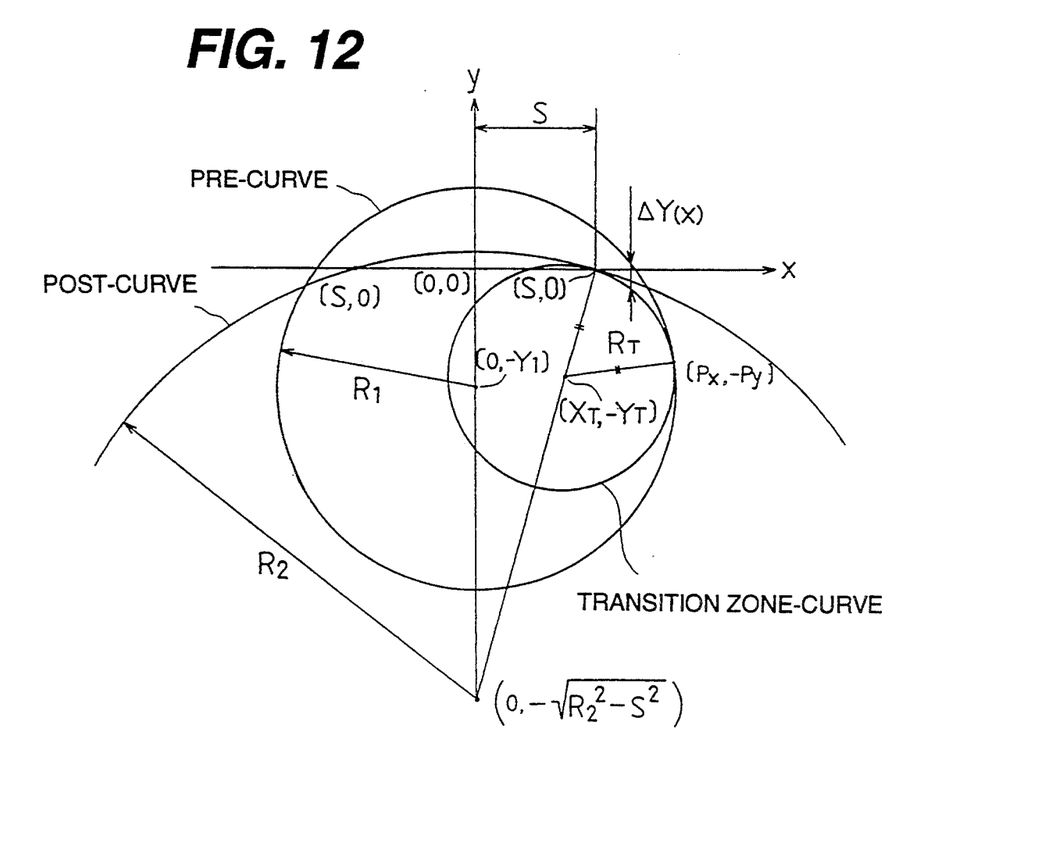
FIG. 12 is a diagram to explain the graphical solution which is basis of the computing the depth of ablation of the transition zone.

The datum $\Delta Y(x)$ is explained according to FIG. 12. The known parameter are two circles which show the curvature of pre-ablation (radius $R_1$) and post-ablation (radius $R_2$), the radius of optical zone S and outer diameter of the transition zone $S_T$. The terminal coordinate of the optical zone is shown as $(x, y) = (S, 0)$ and the coordinate system is set so that the center of the circles of pre-operation and post-operation are positioned on Y-axis.

The equation of the circle having a post-operation's curvature is shown as following formula (8).

$$x^2 + (y + \sqrt{R_2^2 - S^2})^2 = R_2^2 \quad (8)$$

The equation of the pre-operation circle is expressed in following formula (9), when central coordinate is (0, $-Y_1$).

$$x^2 + (y + Y_1)^2 = R_1^2 \quad (9)$$

According to the formula (8), the equation of the circle of the transition zone is shown as following formula (10), because the transition zone's circle is inscribed to the circle shown by formula (8).

$$\left(x - S\frac{R_2 - R_T}{R_2}\right)^2 + \left(y + \sqrt{R_2^2 - S^2}\frac{R_T}{R_2}\right)^2 = R_T^2 \quad (10)$$

In formula (10), $R_T$ shows the radius of the transition zone's circle and is obtained according to the following formula (11).

$$R_T = \frac{(S_T - S)R_1 R_2}{S_T R_2 - S R_1} \quad (11)$$

The coordinate of tangent point which is one between the pre-operation circle and the transition zone's circle is $(P_x, -P) (= (S_T, -P_y))$. According to the formula (9), $Y_1$ is shown as following formula (12).

$$Y_1 = \sqrt{(R_1 - R_T)^2 - \left(S\frac{R_2 - R_T}{R_2}\right)^2} + \sqrt{R_2^2 - S^2}\frac{R_T}{R_2} \quad (12)$$

Accordingly, the distance $\Delta Y(X)$ between the pre-operation circle and the transition zone's circle is obtained as following formula (13).

$$\Delta Y(X) = \sqrt{R_1^2 - X^2} - \sqrt{(R_1 - R_T)^2 - \left(S\frac{R_2 - R_T}{R_2}\right)^2} - \sqrt{R_T^2 - \left(X - S\frac{R_2 - R_T}{R_2}\right)^2} \quad (13)$$

Therefore, $\Delta Y$ at the position of the curved face of the transition zone toward x-axis direction of the coordinate, and the diameter of the aperture is obtained. These operation is proceeded at the arithmetic circuit of the control device 19. When $\Delta Y$ is exceeded over a certain reference value, error message or the like is outputted and it is indicated to change the setting.

The input of the datum is operated by the input device 20 like keyboard, but it is able to connect to the measurement device of the cornea's form. Or it is also able to input the diameter of the curvature of the transition zone, alternate to input the outer diameter of the transition zone such as explained in the above method.

In the above explanation, it is considered to correct the myopia. However, in also case of correcting the myopic astigmatism, it is similarly accomplished by obtaining the shape of the transition zone toward main meridian direction. The correction of the myopic astigmatism is similarly accomplished not only by controlling the width and the length of the slit diaphragm, but also by controlling the angle of inclination of the circular diaphragm.

Figure 13:
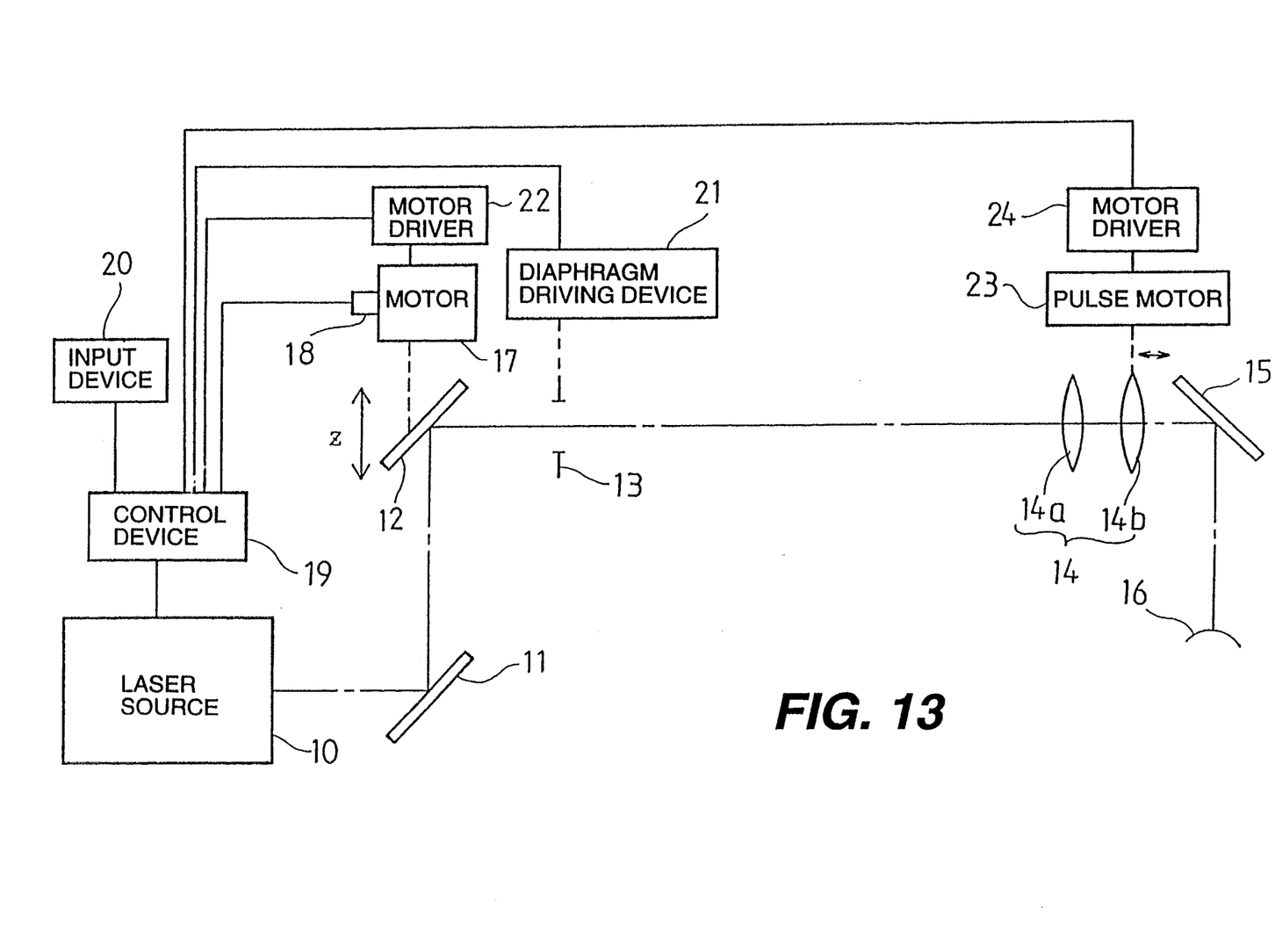
FIG. 13 is a schematic diagram of the arrangement of optical components of the second embodiment of the present invention.

Further, another embodiment is shown in FIG. 13. In the apparatus of this embodiment, which is similarly to that of the first embodiment mentioned above, a projection lens 14 comprises a lens 14a having a focal length fa and a lens 14b which has a focal length fb and is movable in an optical axis direction by a pulse motor 23 via a motor driver 24.

Figure 14:
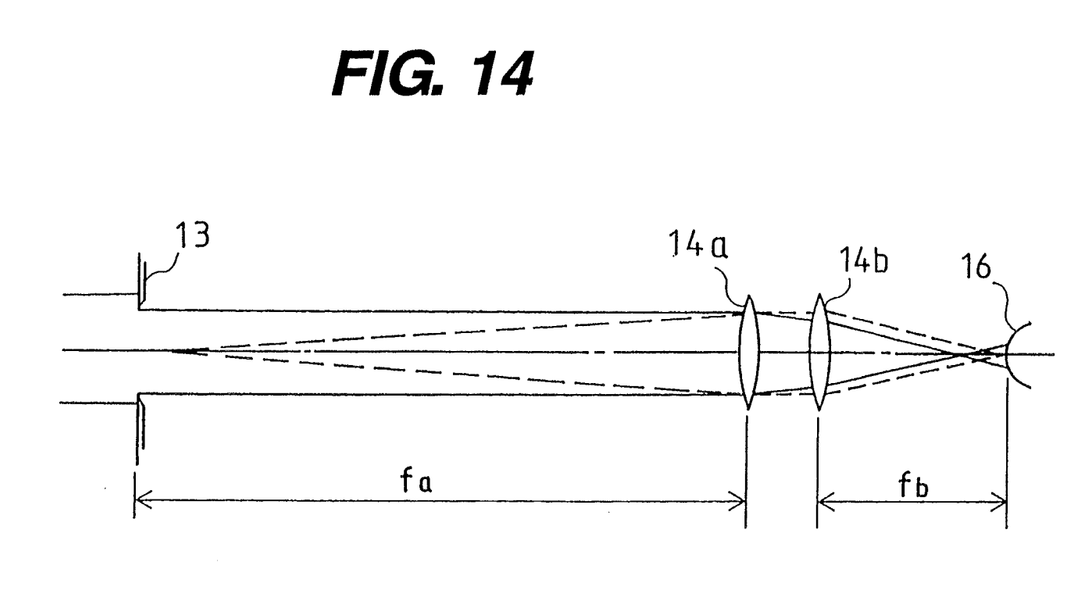
FIG. 14 is a diagram showing the condition of the beam in the second embodiment of FIG. 13.

As shown in FIG. 14, the lens 14a is provided in a position apart from the diaphragm 13 with a focal length fa so that the diaphragm 13 is arranged at the focal point of the lens 14a, and the lens 14b is provided in a position apart from the cornea 16 with a focal length fb so as to locate a surface of the cornea 16 in the focal point thereof, whereby the pencil of rays passed through one point of the diaphragm 13 becomes parallel pencil of rays through the lens 14a, further converges on the surface of the cornea 16 through the lens 14b. When arranged in the above position, the projection lens 14 has the projection magnification $\beta$ being fa/fb.

In considering a practical laser beam, the laser beam of parallel pencil of rays becomes a pencil of Fays having the same form as that of the diaphragm 13 by passing through the diaphragm 13, further condenses at a front of the cornea 16 by passing through lenses 14a and 14b, so that an image of the diaphragm 13 is formed on the surface of the cornea 16.

As that time, the image size formed on the surface of the cornea 16 is determined by calculating a diameter(D) of the diaphragm 13 and a projecting magnification of the projection lens 14, that is, a size of the formed image is obtained according to the formula; $D \times \beta$.

Therefore, a diameter of the laser beam on the cornea 16 is controlled by controlling a diameter of the diaphragm 13, whereby an optical zone of the cornea is ablated to correct a radius of curvature r having an errors of refraction so as to become a radius of curvature r'.

The method of forming the transition zone to connect smoothly an optical zone and a non-ablation area is explained as follows. In this embodiment, the transition zone is formed by controlling an ablation rate.

Figure 15:
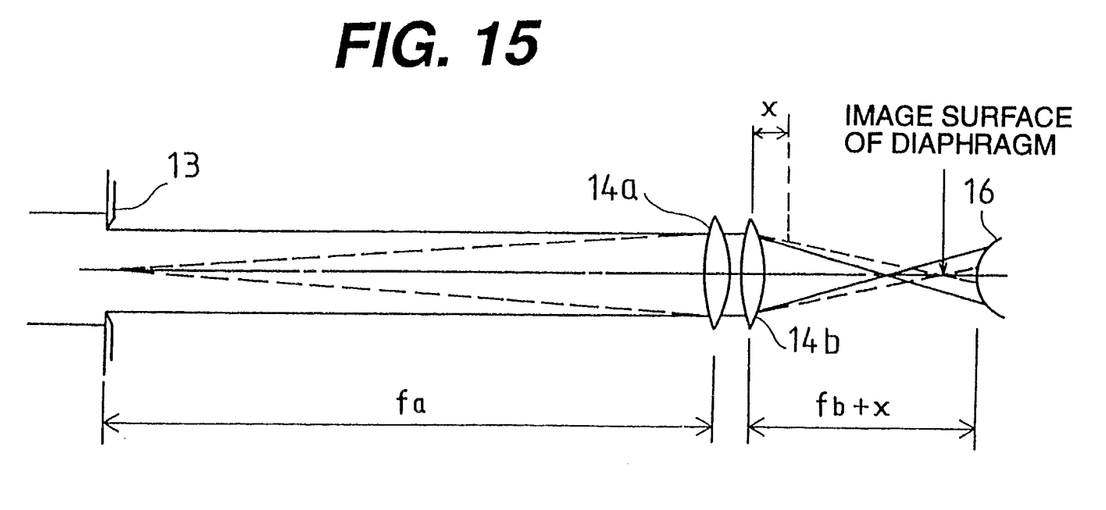
FIG. 15 is a diagram showing the condition of the beam when the lens 14b is moved distance X toward the lens 14a direction.

When moving a lens 14b to a side of a lens 14a with a length x, a distance between the lens 14b and the cornea 16 becomes fa+x, whereby a size of laser beam on the cornea 16 is extended. However, owing to the movement of the image surface of the diaphragm 13 through the projection lens 14 is moved to a front side of the cornea, the outline of the beam on the cornea may be grow dim.

Because the laser beam through the lens must have the same energy regardless of a movement of the lens 14b, a fluence (energy density) of the laser beam on the cornea decrease as an extent of a size of the laser beam thereon after moving the lens 14b, as a result, an ablation rate to ablate a surface of the cornea becomes lower. Therefore, an ablation rate is determined based on the condition of an extent size of the laser beam.

Considering an extent degree of the laser beam, an transition zone is formed so as to connect smoothly an optical zone and non-ablation zone by changing a diameter of the diaphragm 13 and controlling a size of laser beam projected on the cornea.

The transition zone in this case, without drawing a circle precisely calculated as mentioned in the first embodiment, has only to connect an optical zone and non-ablation zone so as not to change the curvature extremely.

The curve of the transition zone is inputted in the apparatus (the computer) as a table related to the radius of curvature before and after correcting the cornea. According to the data, a diameter of the diaphragm 13 is controlled to change a size thereof.

By employing the above mentioned method, it is possible to form the transition zone without deepening the depth of the ablation excessively. Further, instead of a change of a diameter of the diaphragm 13, a change of movement distance of a lens 14b can also reach the same effect.

When employing the method mentioned above, the outline of the laser beam on the cornea is not much clear, but a little dim of the laser beam appeared on the cornea is allowable because it is not exactly necessary to ablate a circle with a precise diameter in the transition zone different from forming an optical zone. In the inventor's experimentation (test), it was confirmed that a diameter of the laser beam is able to be extended on the cornea by moving the lens within the outline of the laser beam being too dim.

Further, although the method for fading the laser beam on the cornea is employed as the easy and effective method to decrease an ablation rate in the above mentioned embodiment, the same effect can be also obtained by employing a method of changing the projecting magnification of the lens by using a zoom lens, or of extending a diameter of the laser beam by moving a diaphragm and a projection lens.

It is also possible to decrease an ablation rate by reducing the energy of the laser beam emitted from the laser source at a beginning or middle point of the optical path, for example, by arranging a filter on the optical path.

The present invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An ablation apparatus for ablating a surface of a cornea to form a transition zone for myopia correction by laser beam, comprising:
    a laser source for emitting a laser beam;
    an ablation optical system for ablating the surface of the cornea by the laser beam emitted from said laser source;
    ablation area changing means for changing an ablation area on the cornea;
    cornea shape forming means for forming a shape of an optical zone of the cornea, the radius of curvature of the shape of the optical zone being larger than the radius of curvature of a pre-operation cornea, by superposing the laser beam through said ablation optical system;
    input means for inputting data related to the transition zone, the transition zone to have a shape for smoothly connecting said optical zone with a non-ablation area; and
    control means for determining the shape of said transition zone, based on the data and based on a curvature of a pre-operation cornea and a desired post operation cornea, and for controlling movement of said ablation area changing means to achieve the shape of the transition zone.

2. The apparatus according to claim 1, wherein said laser source comprises an excimer laser.

3. The apparatus according to claim 1, wherein said ablation area changing means comprises a diaphragm with a variable aperture, and said ablation optical system comprises a projection lens for projecting the laser beam through an aperture onto the cornea.

4. The apparatus according to claim 3, further comprising magnification changing means for changing a projected magnification of said aperture onto the cornea.

5. The apparatus according to claim 4, wherein said magnification changing means comprises movement means for moving said projection lens in the direction of the optical axis so that said aperture is in a non-conjugated position with the cornea to change the ablation area of the cornea.

6. An ablation apparatus for ablating a surface of a cornea by a laser beam comprising:
   a laser source for emitting a laser beam;
   an ablation optical system for irradiating said laser beam emitted from said laser source onto the surface of the cornea;
   ablation area confining means for confining an ablation area on the cornea, said confining means being disposed in said ablation optical system;
   ablation area changing means for changing said ablation area on the cornea confined by said ablation area confining means;
   means for determining a sectional form of a transition zone based on a curvature of a pre-operation cornea and a desired curvature of a post-operation cornea, the transition zone being formed between said ablation area and a non-ablation area; and
   ablation area control means for controlling said ablation area on the cornea to obtain a shape of the transition zone and ensure smooth connection of the transition zone with an optical zone and the non-ablation area.

7. The apparatus according to claim 6, wherein said laser source comprises an excimer laser having an uniform beam intensity in one direction and a non-uniform beam intensity of Gaussian distribution in another direction.

8. The apparatus according to claim 7, wherein said ablation optical system comprises a reflection type optical element for reflecting the laser beam and moving means for moving said reflection-type optical element in the direction of the non-uniform intensity distribution of the laser beam.

9. The apparatus according to claim 8, wherein said ablation area control means controls a range of the ablation area on the cornea each time said reflection type optical element is moved at least one step in a direction of the non-uniform intensity distribution of the laser beam by said moving means.

10. The apparatus according to claim 6, further comprising input means for inputting data relating to the shape of said transition zone, the optical zone, and said non-ablation area; and
   wherein said ablation area control means controls said ablation area changing means based on the data.

11. An ablation apparatus for ablating a surface of a cornea by laser beam comprising:
   a laser source for emitting a laser beam;
   an ablation optical system for ablating the surface of the cornea by the laser beam emitted from said laser source;
   ablation area changing means for changing an ablation area on the cornea;
   cornea shape forming means for forming a shape of an optical zone of the cornea, the radius of curvature of the shape of the optical zone being larger than the pre-operation cornea, by superposing the laser beam through said ablation optical system;
   input means for inputting data related to a transition zone, the transition zone to have a shape for smoothly connecting said optical zone with a non-ablation area; and
   control means for determining the shape of said transition zone, based on the data and based on a curvature of a pre-operation cornea and a desired post operation cornea, and for controlling movement of said ablation area changing means to achieve the shape of the transition zone, wherein the transition zone has a sectional form comprising two circles having a radius, $R_T$, such that:

$$R_T = (s_T - S)R_1 R_2 / (S_T R_2 - S R_1),$$

where $R_1$ is the radius of the pre-ablation zone, $R_2$ is the radius of a post-ablation zone, S is the width of the optical zone, and $S_T$ is the width of the transition zone.

* * * * *